(12) United States Patent
Sugden et al.

(10) Patent No.: US 6,960,429 B2
(45) Date of Patent: Nov. 1, 2005

(54) INHIBITION OF VIRAL GENE ACTIVITIES

(75) Inventors: William M. Sugden, Madison, WI (US); David M. Mackey, Chapel Hill, NC (US)

(73) Assignee: Wisconsin Alumni Research Foundation, Madison, WI (US)

( * ) Notice: Subject to any disclaimer, the term of this patent is extended or adjusted under 35 U.S.C. 154(b) by 41 days.

(21) Appl. No.: 09/808,517

(22) Filed: Mar. 14, 2001

(65) Prior Publication Data

US 2001/0049093 A1 Dec. 6, 2001

Related U.S. Application Data

(63) Continuation-in-part of application No. 08/968,239, filed on Nov. 12, 1997, now abandoned.

(51) Int. Cl.$^7$ .................................................. C12Q 1/00
(52) U.S. Cl. ..................... 435/4; 435/5; 435/6; 435/7.1; 435/7.8; 436/501; 536/23.72
(58) Field of Search ............................ 435/4, 5, 6, 7.1, 435/7.8, 7.92; 436/501, 514, 515, 516; 530/300; 536/23.72, 24.1

(56) References Cited

PUBLICATIONS

Becker et al. Distamycin a inhibition of Epstein–Barr virus replication in arginine–deprived Burkitt lymphoblasts. Isearel Journal of Medical Science (1972) vol. 8, No. 1, pp. 75–78.*

Feriotto et al. Binding of EBV nuclear antigen 1 to DNA inhibition by distamycin and two novel distamycin analogues. European Journal of Pharmacology (1994) vol. 267, pp. 143–149.*

J.E. Mertz, "Linear DNA does not form Chromatin Containing Regularly Spaced Nucleosomes," Mol. and Cel. Biol., 2(12):1608–1618, 1982.

S.A. Stanfield–Oakley et al., Nucleosomal Arrangement of HIV–1 DNA: Maps Generated from an Integrated Genome and an EBV–based Episomal Model, J. Mol. Biol., 256:503–516, 1996.

Q. Gong et al., "Essential Role of NF–E2 in Remodeling of Chromatin Structure and Transcriptional Activation of the E–Globin Gene in Vivo by 5'Hypersensitive Site 2 of the B–Globin Locus Control Region,"Mol. and Cel. Biol., 16(11): 6055–6064, 1996.

J. Cote et al., "Perturbation of Nucleosome Core Structure by the SWI/SNF Complex Persists After its Detachment, Enhancing Subsequent Transcription Factor Binding," Proc. Natl. Acad., 95:4947–4952, 1998.

G. Orphanides, et al., "FACT, a Factor that Facilitates Transcript Elongation Through Nucleosomes," Cell 92:105–116,1998.

D. Mackey and B. Sugden, "The Linking Regions of EBNA1 are Essential for Its Support of Replication and Transcription," Mol. Cell. Biol. 19(5):3349–3359, 1999.

* cited by examiner

*Primary Examiner*—Ulrike Winkler
(74) *Attorney, Agent, or Firm*—Quarles & Brady LLP

(57) ABSTRACT

A method of inhibiting viral gene activities (and cellular gene activities) is disclosed. In one embodiment, the method comprises the step of delivering an effective amount of an inhibitor of a viral looping/linking factor to an infected patient.

5 Claims, 4 Drawing Sheets

B

C

INHIBITION OF VIRAL GENE ACTIVITIES

CROSS-REFERENCE TO RELATED APPLICATION

This application is a continuation-in-part of U.S. Ser. No. 08/968,239 filed Nov. 12, 1997, now abandoned, which is incorporated by reference herein.

Not applicable.

STATEMENT REGARDING FEDERALLY SPONSORED RESEARCH OR DEVELOPMENT

This invention was made with United States government support awarded to the following agency: NIH CA07175; CA22443; CA70723. The United States has certain rights in this invention.

BACKGROUND

The Epstein-Barr virus (EBV) infects human B-lymphocytes and usually establishes a latent infection in them. In vivo and in vitro, the latently infected cells are induced to proliferate. Interestingly, the viral genome is maintained in these cells as a plasmid which is both replicated conservatively during S-phase and maintained efficiently at a stable copy number (1, 2, 3, 4). Only one of the latent viral gene products, EBNA1, and a small (1.8 kbp) cis-acting element (oriP) are required to recapitulate faithful plasmid replication in human and some other cells (5, 6, 7). Replication of oriP plasmids provides a useful model for studying control of initiation of replication, segregation of replicated DNAs, and maintenance of those DNAs in the mammalian nucleus.

Dimers of EBNA1 bind specifically to degenerate, 20 bp-sequences of DNA (8). The carboxy-terminal one-third of EBNA1 contains the residues sufficient for both dimerization and DNA-binding (FIG. 1) (9, 10, 11, 12). (By "dimerization of EBNA1" we refer to protein:protein interactions between the DNA-binding domain of EBNA1, and not to protein:protein interactions between linking domains.) The EBV genome contains twenty-six identified sites to which EBNA1 binds (13). Twenty-four of these sites are within two clusters which comprise oriP (5). Twenty sites with a high affinity for EBNA1 are embedded within a series of 30 bp repeats, termed the family of repeats (FR). The dyad symmetry element (DS), which is located 1 kbp away from FR contains four binding-sites for EBNA1 with lower affinity than those in FR, two of which are part of a 65 base pair dyad (5, 14, 8, 15, 29). The DS is required for replication of oriP and is the site at which or close to which DNA synthesis initiates (Gahn and Schildkraut, 1989). EBNA1, when bound to FR, can activate transcription of two viral promoters, one of which is ten kbp away (16, 17, 18). The ability of EBNA1 to bind to DNA is essential for its activation of replication and transcription through oriP (19, 20).

In addition to binding to FR and DS, EBNA1 can also link them, forming a loop of the intervening DNA (21, 22). Activities of EBNA1 other than DNA-binding and DNA-linking have not been identified. EBNA1 purified from insect and mammalian cells lacks detectable helicase or ATPase activity (23, 24). EBNA1's apparent lack of enzymatic activities led several labs to search for proteins with which EBNA1 can interact. No candidates that obviously contribute to the function of EBNA1 have been identified.

One study demonstrated that no small deletion within EBNA1, other than those which affect DNA-binding, abrogates the ability of EBNA1 to activate transcription or replication (19). The authors interpreted this finding to indicate that EBNA1 contains redundant activating domains. The linking domains of EBNA1 are redundant and therefore are reasonable candidates for its activating domains. Findings in another study, which show a correlation between the presence of linking domains and the activity of derivatives of EBNA1, support this contention (25).

SUMMARY OF THE INVENTION

In one embodiment, the present invention is a method of inhibiting or diminishing viral infection. Most preferably, this method comprises the step of delivering an effective amount of an inhibitor of a viral looping/linking factor to an infected patient, wherein the viral looping/linking factor is derived from the same virus as the infecting virus.

In a most preferred form of the method, the viral infection is Epstein Barr Virus infection. In another preferred form of the invention, the viral infection is selected from the group consisting of Epstein Barr Virus, Human Papilloma Virus, and Herpes Simplex Virus infection.

In a preferred embodiment, the inhibitor is a peptide. Preferably, if one wishes to inhibit or diminish EBV infection, the peptide comprises EBNA1 residues 40–89 or 331–391. Most preferably, the peptide comprises EBNA1 residues 54–89, 331–361 or 372–391. The inhibitor may also comprise a small molecule, such as peptidomimetics, identified in a high through-put screen.

In another embodiment, the present invention is a method of screening for viral inhibitors comprising the step of determining whether a candidate molecule inhibits protein-:protein linking of a viral looping/linking factor. In a most preferable form, the assay is either a gel shift assay or a promoter activation assay, both described in detail below.

In another embodiment, the present invention is a method of modulating protein:protein interactions comprising the step of exposing a cellular looping/linking factor to an inhibitor. Preferably, the cellular looping/linking factor is selected from the group consisting of Sp1, NtrC, n and Pit-1.

It is a object of the present invention to diminish viral infection in an infected patient.

It is another object of the present invention to disrupt the action of the action of viral looping/linking factors.

It is another object of the present invention to disrupt cellular looping/linking factors.

Other objects, features and advantages of the present invention will become apparent after review of the specification, claims and drawings.

DESCRIPTION OF THE DRAWINGS

FIG. 3A is a scan of electrophoretic gel demonstrating a gel shift assay.

DESCRIPTION OF THE INVENTION

1. In General

Figure 1:
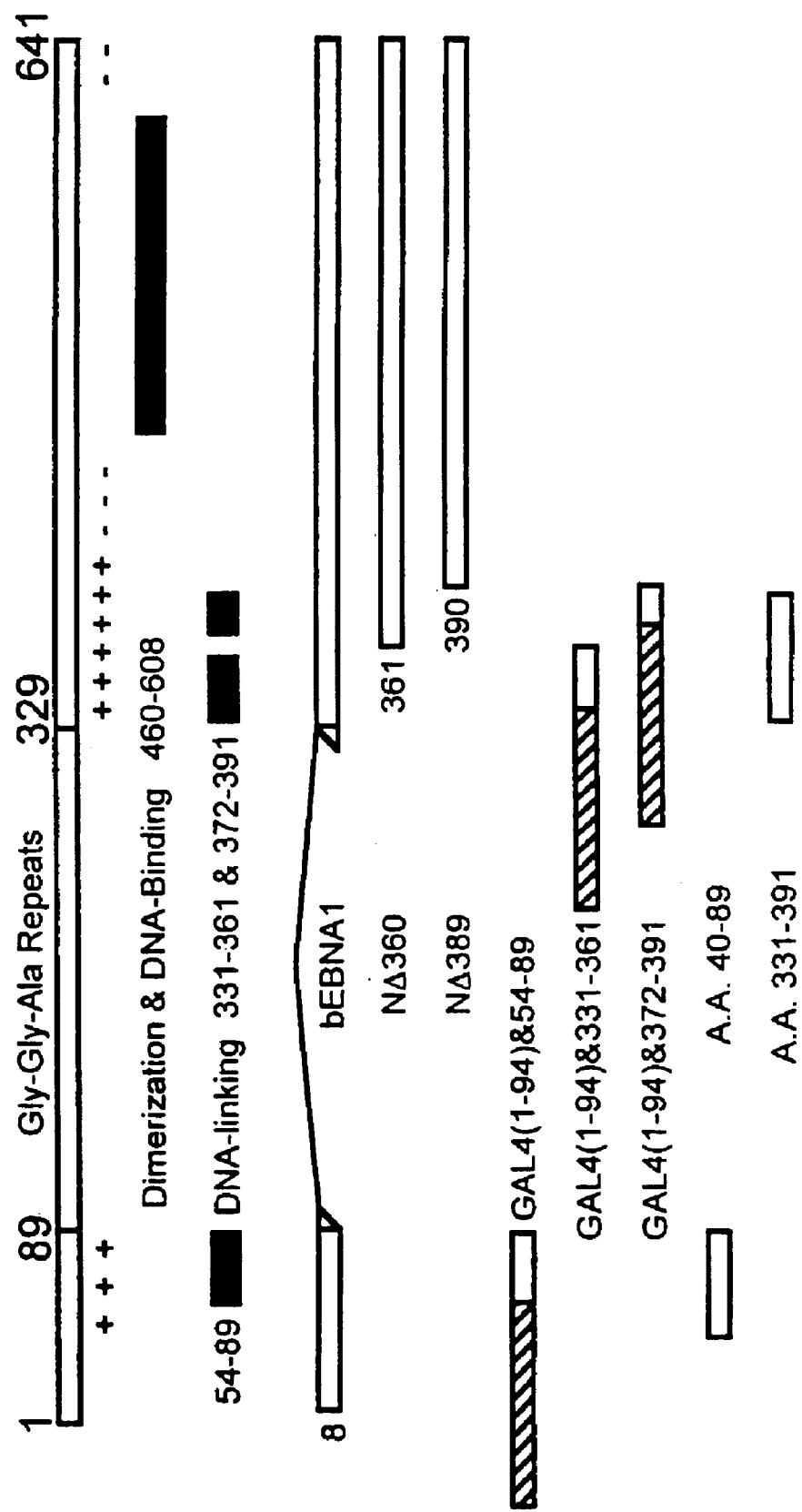
FIG. 1 is a schematic representation of EBNA1 and its derivatives used in the Examples.

EBNA1 can form intramolecular loops between FR and DS and can also intermolecularly link DNAs to which it binds (21, 22, 24, 26, 27, 28). We have studied linking primarily in electrophoretic mobility shift assays (gel shifts) (28). Multiple derivatives of EBNA1 behave similarly in gel shift assays and three other described linking assays (26, 28).

In a gel shift assay, DNAs linked by EBNA1 do not migrate appreciably into a 4% polyacrylamide gel. The efficiency with which a DNA is incorporated into a linked complex increases with the number of EBNA1-binding sites it contains, but linking of DNAs containing only one site can be detected.

We have identified three regions of EBNA1, amino acids 54–89, 331–361, and 372–391, which mediate DNA-linking. When fused to the dimerization and DNA-binding domain of GAL4 these fragments of EBNA1 mediate linking of DNAs containing five GAL4-binding sites. We also observed that increasing concentrations of linking protein decrease the efficiency of linking. This phenomenon, reminiscent of dissolution of antibody:antigen complexes by excess antigen, indicates that protein:protein interactions between the linking domains may underlie linking. We have tested this hypothesis.

We have found that protein:protein interaction between linking domains can mediate linking. Because linking domains of EBNA1 function when fused to the exogenous DNA-binding protein, GAL4, models in which a linking domain interacts specifically with a DNA-binding domain cannot be supported. Rather, linking is mediated by protein-:protein interactions between the linking domains themselves.

The efficiency of DNA-linking mediated by EBNA1 increases and then decreases as the concentration of EBNA1 increases relative to the DNA bound by it. Inhibition of linking is observed at concentrations of EBNA1 which are in excess relative to the EBNA1 bound to DNA site-specifically, but are far less than the total DNA in the reaction. This observation indicates that the inhibition of linking is mediated by protein:protein interactions. Also consistent with this interpretation are our findings that proteins which contain linking domains can efficiently inhibit DNA-linking and that peptides from EBNA1 which contain only linking domains can similarly inhibit linking. We also determined whether nucleic acids other than those bound site-specifically by EBNA1 are essential for linking, and they are not. These results demonstrate that EBNA1 can link DNAs by protein:protein interactions between its linking domains.

The method of the present invention begins with our observation that the protein:protein linking that loops out intervening DNA is a more accessible antiviral target than the protein:DNA binding reaction between EBNA1 and DNA sites. We refer to the proteins that mediate this linking as a "viral looping/linking factor." Protein:protein linking can be inhibited without inhibiting the related protein:DNA binding. The Examples below describe inhibition of protein:protein linking by peptides containing the linking domain sequence.

Therefore, in one embodiment the present invention is a method of inhibition of viral replication by disruption of EBNA1-mediated DNA-linking. In many cases, inhibition of viral replication equates with inhibition of tumor formation. The method comprises the step of delivering an effective amount of an EBNA1 linking inhibitor to the infected patient, thus disrupting EBNA1 linking and viral replication. As the Examples below describe the residues of EBNA1 that mediate linking, one may design a very specific peptide inhibitor.

In another embodiment, the present invention is a method of measuring inhibition of protein:protein linking as a means for screening for antiviral compounds.

In another embodiment, the present invention is a method for inhibiting replication of other viruses which utilize linking/looping during the replication cycle.

In another embodiment, the present invention is a method of modulating linking/looping activity in other cellular contexts.

2. Inhibition of EBV Replication

Inhibitors of EBNA1's DNA-linking functions will have clinical value because EBNA1 is the only EBV protein expressed in all diseased cells infected with EBV and is, therefore, a good candidate for antiviral therapy. The Examples below demonstrate specific peptides that can inhibit DNA-linking mediated by EBNA1 in vitro. For example, peptide inhibitors comprising the following amino acids of EBNA1 would be preferable inhibitors: A.A.s 40–89, 331–391, 54–89, 331–361, and 372–391. However, we envision that other peptides and small molecules may also inhibit DNA linking by EBNA1. The small molecules will most likely be peptidomimetics that mimic the action of EBNA1 residues described below. Because EBNA1 residues 40–89 and 331–391 are highly basic, we envision that the most successful competitive inhibitors will also be basic in charge.

Applicants note that the amino acid residues of EBNA1 are numbered according to reference 15 (Baer, et al., 1984, *Nature* 310:207–211). This reference is incorporated by reference as if fully set forth herein.

Applicants envision that a preferable length of a peptide inhibitor will be between 18–22 amino acid residues in length, preferably 20 residues in length. However, we envision that both smaller and larger peptides will prove to be suitable.

By "inhibition of DNA linking" we mean that the inhibitor has a $K_i$ (defined below) of no more than twice that of the peptide inhibitors that we examine below (A.A. 40–89 and A.A. 331–391) at disrupting EBNA1's linking activities. Preferably the $K_i$ of the inhibitor is at most equivalent to that of the peptides described above.

Applicants envision that one may wish to determine whether candidate inhibitor molecules are suitable for the present invention.

The Examples below disclose a gel shift assay as a typical method of determining whether a particular molecule inhibits DNA-linking by EBNA1. Applicants envision a more direct method as follows: Proteins that activate transcription do not function unless they are in close proximity to the promoter. A promoter that is inactive without activation (minimal promoter) will be placed several kilobase pairs from binding sites for a transcriptional activator.

We envision using binding sites for GAL4. Thus, we will use GAL4 fused to the activation domains of various transcription factors.

Binding sites for EBNA1 will be juxtaposed to both the minimal promoter and to the binding sites for the transcription factor. DNA-linking of these sites by EBNA1 will bring the binding sites for the transcription factor in a position relative to the promoter which results in its activation.

This scheme would be confounded if EBNA1 itself activated transcription. EBNA1 has been shown not to activate transcription in yeast, and activates transcription in mammalian cells only when at least six binding sites are present.

The NΔ360-derivative of EBNA1 described below can efficiently link DNA and will be tested for its ability to activate the promoter just described. If activation of the promoter is observed, peptides containing linking domains, which efficiently inhibit DNA-linking by NΔ360, will be tested for their ability to disrupt this activation.

This experimental system will be used to screen compounds for their ability to inhibit DNA-linking by EBNA1. An advantage of conducting the screen in mammalian cells is that the mammalian cell system can control for toxicity and drug up-take.

By the method of the present invention, one delivers an effective amount of a viral linking/looping inhibitor to an infected patient, thus diminishing or inhibiting viral infection.

3. Inhibitors of Other Viruses

We envision that the method of the present invention will be equally suitable for inhibition of other viruses that rely on DNA looping/linking during replication. Specific examples of DNA looping/linking proteins which are required for viral replication are listed below in Table 1.

TABLE 1

| Virus | Linking Protein | Reference/Description |
| --- | --- | --- |
| Papilloma virus | E2 | Knight, et al., PNAS 88:3204–3208 (1991); Li et al., .Cell 65:493–505 (1991). |
| Herpes Simplex Virus | UL9 | Koff, ets al., J. Virol. 65:3284–3292 (1991). |
| Adenovirus | pTP | Robinson, et al., Virology 56:54–69 (1973). |

Each of these proteins has been shown to loop DNAs to which it binds. UL9 is required for herpes simplex virus (HSV) replication in cells. E2 is required for human papilloma virus replication in cells and also activates viral transcription.

To practice the method of the present invention, one would first develop inhibitors of viral DNA looping/linking proteins, such as E2, UL9 and pTP, by methods described below in the Examples. This method would allow one to map particular linking domains and to develop specific inhibitors that would block association at these domains.

With this information in hand, one could then deliver the inhibitor to an infected patient, as described above.

4. Inhibition of Other Proteins with Looping/Linking Activity

Table 2 lists other proteins with looping/linking activity:

TABLE 2

| Protein | Referenced Description |
| --- | --- |
| Sp1 | Su, et al., Gene. & Dev. 5:820–326 (1991); Li, et al., Cell 65:493–505 (1991). Mammalian transcription factor. |
| NtrC | Schleif, R., et al., Ann. Rev. Biochem. 61:199–223 (1992). Bacterial transcription factor. |
| π | Schleif, R., et al., Ann. Rev. Biochem. 61:199–223 (1992). Replication initiator protein of the bacterial plasmid R6K. |
| Pit-1 | Cullen, et al., Science 261:203–206 (1993). Mammalian transcription factor. |

One could use the method of the present invention to modulate the looping/linking activity of other cellular proteins, most preferably those listed above in Table 2.

5. Identification of Viral Replication and Transcription Inhibitors

In one embodiment, the present invention is a method of screening prospective viral replication inhibitors and viral transcription inhibitors. The method would determine whether a candidate molecule could inhibit the viral looping/linking factor, as demonstrated by the factor being unable to mediate DNA linking in the presence of a candidate molecule.

In a preferred embodiment, one would add a candidate molecule to a mammalian cell culture, wherein the cell culture comprises a viral looping/linking factor. One provides a control mammalian cell culture, also comprising a viral looping/linking factor, one allows the candidate molecule to interact with the viral looping/linking factor present in the mammalian cell culture. One then analyzes the factor for inhibition by the candidate molecule, and then compares the results using the control culture, wherein the candidate molecule inhibits protein:protein linking as demonstrated by the factor being unable to mediate DNA linking in the presence of the candidate molecule.

Applicants have described below one example of a system of plasmids designed to determine whether a candidate molecule could inhibit the viral looping/linking factor. Of course, other suitable promoters and markers would be apparent to one of skill in the art of molecular biology.

One such assay would use DNA-linking to loop out intervening DNA between two distant binding sites for EBNA-1 such that juxtaposition of those sites would bring a transcriptional activator adjacent to a promoter. DNA-linking would activate transcription which would be monitored by a surrogate such as luciferase activity. Small molecules that inhibit DNA-linking would score in this assay by decreasing the measured luciferase activity.

The concentrations of small molecules which are candidates for inhibitors of DNA-linking would be varied in these cell-based assays because their affinities for EBNA-1's linking domains cannot be known a priori. However, one instructive starting point for the concentrations to be tested can be gleaned from the measured inhibitory constants of peptides consisting of either of EBNA-1's linking regions needed to inhibit linking to EBNA-1 in vitro. The Ki (concentration needed for 50% inhibition) for these two peptides for linking by one studied derivative of EBNA-1 has been measured to be 30–50 nanomolar (Mackey and Sugden, J. Biol. Chem. 272:29873–29879, 1997). This measurement indicates that the concentrations of small molecules to be tested in a cell-based assay for DNA-linking should range between $10^{-6}$ and $10^{-8}$ molar.

For example, to identify molecules that inhibit linking mediated by EBNA-1, a plasmid encoding renilla luciferase driven by a minimal thymidine kinase promoter could be constructed. Upstream of the promoter could be placed two binding sites for EBNA-1, then ten kilobase pairs of lambda phage DNA, then two binding sites for EBNA-1, and then eight binding sites for the Ga14 yeast DNA-binding protein. The remainder of the plasmid could contain the β lactamase gene, the Colicon E1 origin of replication, and a puromycin resistance gene expressed from an SV40 early promoter followed by an SV40 polyadenylation signal.

This DNA could be linearized within the β lactamase gene, introduced into 293 cells by transfection using calcium phosphate and the cells selected with 1 microgram per ml of puromycin. After 14 days of selection, resistant cells could be isolated, expanded to $10^7$ cells, and screened by Southern blotting for those clones in which the transfected DNA has been integrated as an intact, linear molecule.

The resulting clones (termed "parental test clones") could then be screened to identify the "ultimate test clone" as follows: The parental test clones will be transfected via calcium phosphate first with a plasmid expressing a fusion protein consisting of the Gal4 DNA-binding domain fused to the herpes simplex type 1 VP16 transactivation domain. Clones that show a minimal increase of luciferase activity 48 hours later (less than two-fold) could be studied further. Those clones to be studied further could then be transfected with a plasmid expressing the Gal4-VP16 fusion protein and one expressing EBNA-1. Those transfected clones which show an increase in luciferase activity of at least ten-fold 48 hours later than that induced by expression of the Gal4-VP16 fusion protein alone will be studied further. They will be transfected with a plasmid expressing a derivative of EBNA-1 containing its DNA-binding domain fused to the transactivation domain of VP16.

Cells in which luciferase activity is induced ten-fold or greater 48 hours later by virtue of EBNA-1's DNA-binding domain tethering the activation domain of VP16 immediately upstream of the thymidine kinase promoter will be studied further. The clone that responds most efficiently in luciferase activity to co-expression of Gal4-VP16 plus EBNA-1 relative to co-expression of Gal4-VP16 plus the derivative of EBNA-1 lacking linking domains would be used further and termed the "ultimate test clone (UTC)."

To identify compounds that inhibit linking specifically, one set of UTC cells could be transfected with expression vectors for Gal4-VP16 plus EBNA-1 (Set 1) and another set with the expression vector for the EBNA-1 DNA-binding domain fused to Gal4-VP16 (Set 2). These cells will be plated into 96 well plates at $10^4$ cells per well. Twenty-four hours later they would be transfected with a range (1 ng to 50 μg) of a plasmid in which linking region 1 of EBNA-1 is expressed from the human CMV immediate early promoter (test plasmid). The level of expression vector which reduced the renilla luciferase (the substrate can be added to live cells) activity by 50% or more in Set 1 without affecting the luciferase activity in Set 2 would preferably be used in subsequent experiments. Experiments in Set 2 control for any non-specific toxicity resulting from transfected DNA or treatment with other compounds to be tested.

To identify the smallest peptide capable of inhibiting linking, the insert in the test plasmid will be systematically shortened, one coding triplet per step, independently from the amino and carboxy termini of linking region 1. This family of plasmids will be tested in UTC cells as described above for intact linking region 1. The identification of the smallest domain within linking region 1 that inhibits linking with UTC cells specifically will enable modeling of peptidomimetic compounds to be added extracellularly to inhibit linking by EBNA-1 within cells. Such lead compounds will be tested in the UTC cells in treated Set 1 and Set 2 experiments.

Once one has created the appropriate UTC cells, one would then be able to expose the UTC cells to test compounds and measure DNA linking, preferably as described in the Examples.

EXAMPLES

DNAs

Two DNAs used as probes in this study were generated by endonuclease digestion of cloned DNAs. That with two EBNA1-binding sites is the 131 bp, SalI to PstI fragment derived from p880 (30); and that with five GAL4-binding sites is the 109 bp, HinDIII to XbaI fragment derived from G5BCAT (31). DNA fragments were purified from agarose gels. They were quantified by making serial dilutions in the presence of ethidium bromide (0.5 μg/mL) and comparing their intensities, when exposed to ultraviolet light, to that of similar dilutions of a standard DNA. This method distinguishes less than two-fold differences in DNA concentrations. These DNAs were labeled with the Klenow fragment of DNA Polymerase 1 in the presence of dATP, dGTP, dTTP, and $^{32}$P α-dCTP (Amersham), and precipitated three times to remove unincorporated label (32).

Proteins

The derivatives of EBNA1 (bEBNA1, NΔ360, NΔ389) and the GAL4 derivatives (GAL4(1–94), GAL4(1–94) &54–89, GAL4(1–94)&331–361, GAL4(1–94)&372–391) used in this study were all produced and purified as previously described (28). Briefly, bEBNA1 lacks amino acids 2 through 7 and all but fifteen amino acids of the gly-gly-ala repeats and was expressed in SF21 cells (23). NΔ360 and NΔ389 lack the first 360 and 389 amino acids, respectively, and were expressed in *E. coli*. GAL4(1–94) contains amino acids 1 to 94 of the yeast transactivator GAL4 plus eight carboxy-terminal amino acids coded by the poly-cloning region. The fusions designated GAL4(1–94)&#—# contain the indicated residues from EBNA1 cloned in frame into the poly-cloning region. All derivatives and fragments of EBNA1 were derived from the B95-8 viral strain (33, 15).

A.A. 40–89 and A.A. 331–391 were generated by amplifying the fragment of EBNA1 encoding those amino acids with PCR primers containing SalI and XbaI sites at the 5' ends. Cloning of these fragments into the SalI and XbaI sites of pET-23b+ (Novagen) resulted in fusions encoding an epitope (T7•Tag, Novagen), the EBNA1 amino acids, and 6 histidines. The sequence of both clones was verified using an ABI Prism automated sequencer (Applied BioSystems). Expression of the fusion proteins in BL21 bacteria containing a DE3 lysogen and carrying pLysS was done as previously described (28). Purification using $Ni^{2+}$-NTA agarose (Qiagen) followed standard protocols (The QIAexpressionist, Qiagen). Following elution of A.A. 40–89 and A.A. 331–391 in 500 and 150 mM imidazole, respectively, the peptides were dialyzed into a buffer containing 50 mM Tris (pH 7.5), 2.5 mM EDTA, and 0.3 M NaCl.

Electrophoretic Mobility Shift Assays

Gel shift assays were done as previously described (28). All reactions contained 20 mM N-2-hydroxyethylpiperazine-N'-2-ethanesulfonic acid (HEPES; pH 7.6), 2 mM EDTA, 10% glycerol, 0.1% Nonidet P-40, and 0.3 M NaCl. Proteins were mixed in volume of 15 μl. The labeled DNA and 3 μg of poly(dI)•poly(dC) (Pharmacia) in 8 μl were added with mixing. The reactions were then incubated 30–45 minutes at room temperature. Reactions were separated by electrophoresis at 15–25 mA through a 4% polyacrylamide gel in 0.5×TBE (45 mM Tris-borate and 1 mM EDTA). Gels were dried on 3MM chromatography paper (Whatman) at 80° C. for 1 hour and then exposed to phosphorimager screens. The percentage of DNA linked is determined by dividing the amount of linked DNA by the total amount of DNA in the lane.

Results

Effect of Linking Domains on the Efficiency of DNA-linking—DNA-linking by EBNA1 is inhibited at increasing concentrations of EBNA1 (28). Fusions of the DNA-binding domain of GAL4 and individual linking domains of EBNAL also link DNAs containing GAL4-binding sites less efficiently as their concentration is increased beyond that required to yield maximal linking. We tested whether each type of linking protein could inhibit linking by the other type. FIG. 1 is a schematic representation of EBNA1 and its derivatives used in this study. EBNA1 from the prototypical B95-8 viral strain is depicted at top. The plus signs (+) and minus signs (−) represent regions rich in basic and acidic residues, respectively. The gly-gly-ala repeats extend from position 90 to 328 and contain exclusively glycines and alanines. Shaded boxes indicate the portion of EBNA1 required for dimerization and DNA-binding and the positions of the three identified DNA-linking domains. Below, portions of EBNA1 used in this study are positioned such that the EBNA1 sequences (unfilled bars) are aligned with their corresponding sequence in full-length EBNA1. bEBNA1 starts with a methionine followed by amino acid 8 and contains 15 amino acids of the gly-gly-ala repeats. NΔ360 and NΔ389 have a methionine followed by amino acids 361 and 390 to the carboxy-terminus, respectively. The diagonally striped bars represent amino acids 1 to 94 of GAL4. A.A. 40–89 and A.A. 331–391 each have an epitope tag at the amino-terminus and 6 histidines at the carboxy-terminus.

FIGS. 2A and B are bar graphs demonstrating that inhibition of DNA-linking is mediated by linking domains. The ability of GAL4(1–94)&54–89 (FIG. 1) to link DNAs containing five GAL4-binding sites was tested in the absence of any competitor and in the presence of a 2.5-fold molar excess of three derivatives of EBNA1 (FIG. 1). EBNA1-derivatives which can link DNA inhibit linking by GAL4 (1–94)&54–89, those which cannot link DNA do not inhibit linking by GAL4(1–94)&54–89. Similarly, DNA-linking by EBNA1 is only inhibited by derivatives of GAL4 fused to linking domains. GAL4(1–94) does not inhibit linking by NΔ360, derivatives of GAL4(1–94) fused to three separate linking domains of EBNA1 can inhibit linking by NΔ360. FIG. 2A: 10 fmols of a DNA with five GAL4-binding sites were combined with 400 fmols of dimers of GAL4(1–94) &54–89 and 1000 fmols of dimers of the indicated competitor. In one experiment the reactions contained 10 fmols of an unlabelled DNA containing 10 EBNA1 binding sites. The presence of this DNA makes no detectable difference. FIG. 2B: 20 fmols of a DNA with two EBNA1-binding sites were combined with 150 fmols of dimers of NΔ360 and 675 fmols of dimers of the indicated derivatives of GAL4. For both FIGS. 2A and B the reactions were manipulated and analyzed to determine the percentage of maximum DNA linked as in FIG. 3. The amount of DNA linked in the absence of competitor protein is set to 100% and was 15% for NΔ360 and 22% for GAL4(1–94)&54–89. The percentage linked of this maximum is shown for the various competitors. The standard deviations are from two separate experiments.

Derivatives of EBNA1 which contain linking domains, bEBNA1 and NΔ360, inhibited linking by the GAL4 (1–94)+54–89 (FIG. 2A). NΔ389, which cannot link DNA, failed to inhibit linking by the fusion protein (FIG. 2A). The converse experiment was also conducted (FIG. 2B). The ability of NΔ360 to link DNAs containing two EBNA1-binding sites was tested in the absence of any competitor and in the presence of a 4.5-fold molar excess of four GAL4-derivatives (FIG. 1). Derivatives of GAL4 fused to linking domains of EBNA1, GAL4(1–94)&54–89, GAL4(1–94) &331–361, and GAL4(1–94)&372–391, inhibited linking by NΔ360. Unfused GAL4(1–94) did not inhibit linking by NΔ360. In these experiments there was a direct correlation between proteins that can inhibit DNA-linking and proteins that contain DNA-linking domains.

Effect of Peptides Containing Linking Domains on DNA-linking by EBNA1

The observation that proteins with linking domains could inhibit DNA-linking led us to test whether linking domains alone would be sufficient to inhibit DNA-linking by EBNA1. For most experiments NΔ360, which contains only one linking domain, was studied to facilitate detection of inhibition of linking. Two DNAs encoding fragments of EBNA1 (residues 40–89 and 331–391, FIG. 1) were cloned into plasmids allowing efficient protein expression in bacteria. These fragments include all the amino acids from EBNA1 which are likely to contribute to DNA-linking (28, 34). The fragments of EBNA1 are fused at their amino-terminus to an epitope and at their carboxy-terminus to 6 consecutive histidines. The epitope allowed identification of the desired peptides, and the 6-His tag facilitated their purification. Both peptides (A.A. 40–89 and A.A. 331–391) were purified to near homogeneity and tested for their ability to inhibit DNA-linking.

Figure 3A:
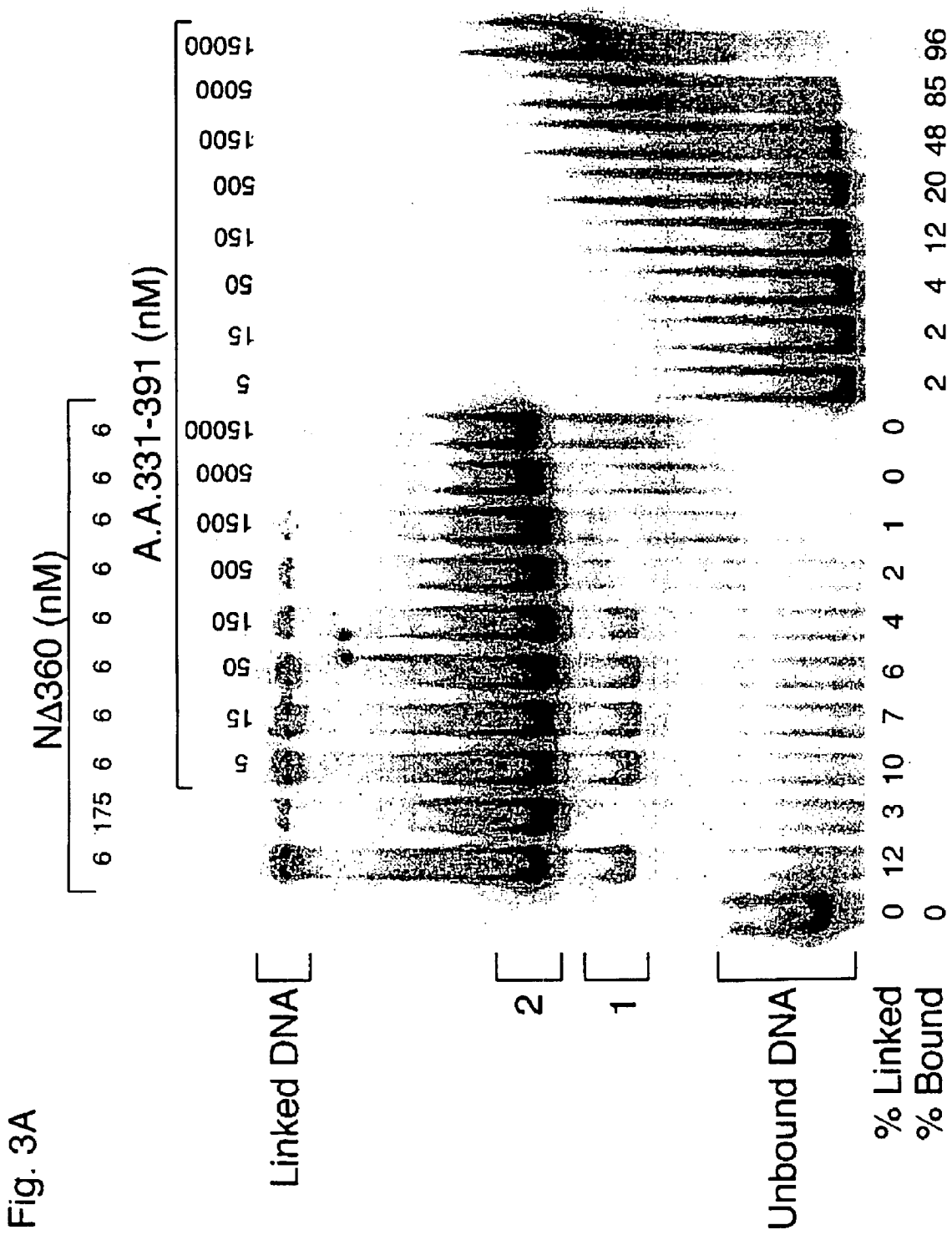
FIGS. 3A, B and C demonstrates that fragments of EBNA1 containing linking domains can inhibit DNA-linking by NΔ360.

A.A. 40–89 and A.A. 331–391 can each inhibit DNA-linking. FIGS. 3A, B and C demonstrate that fragments of EBNA1 which contain linking domains can inhibit DNA-linking by NΔ360. The concentrations of the peptides required to inhibit DNA-linking are significantly lower than the concentrations at which the peptides bind to DNA. FIG. 3A: 20 fmols of a DNA with two EBNA1-binding sites were combined with the indicated concentrations of dimers of NΔ360 and A.A. 331–391 prior to separation by electrophoresis through a 4% polyacrylamide gel. Linked DNA is incorporated into complexes too large to migrate significantly into the gel. The positions of linked DNA, unbound DNA, and DNA with one and two sites occupied by NΔ360 (1 and 2, respectively) are indicated. Phosphorimage analysis was used to calculate the percentage of linked DNA by dividing the amount of linked DNA by the total DNA in each lane, and this percentage is displayed at bottom. The percentage bound is the fraction of the total DNA in the lane which is shifted above the bracket for unbound DNA. FIGS. 3B and 3C: Graphical representations of the ability of A.A. 331–391 (B) and A.A. 40–89 (C) to inhibit linking by 6.5 nM of dimers of NΔ360 and to bind to DNA in the absence of NΔ360. The concentrations of A.A. 331–391 and A.A. 40–89 required to reduce linking to 50% of that in the absence of competitor are 2% and 1% of the concentration of each required to bind 50% of the DNA, respectively. The standard deviations are from three separate experiments.

The efficiency with which NΔ360, a derivative of EBNA1 with only one linking domain, links DNAs containing two EBNA1-binding sites was measured in the presence of a range of concentrations of A.A. 331–391 (FIG. 3A). The same range of concentrations of A.A. 331–391 was also tested in the absence of NΔ360. A.A. 331–391 can both inhibit NΔ360-mediated DNA-linking and, because of its high positive charge, bind to DNA. However, its inhibition of linking occurred at a significantly lower concentration than did its DNA-binding. Similar experiments were conducted for A.A. 40–89 and the results for A.A. 331–391 and A.A. 40–89 are represented graphically in FIGS. 3B and 3C, respectively. The concentration of each peptide which reduced linking to 50% of that in the absence of competitor ($K_i$) was significantly less than the concentration which bound 50% of the DNA. These concentrations differ by 50 and 100-fold for A.A. 331–391 and A.A. 40–89, respectively. These experiments demonstrate that A.A. 331–391 and A.A. 40–89 can inhibit linking independently of their ability to bind to DNA. Even high concentrations of the peptides, which bind DNA detectably in gel shift assays, do not displace NΔ360 bound specifically to the probe DNA (FIG. 3A and data not shown).

The inhibition of linking mediated by A.A. 331–391 and A.A. 40–89 is specific. The peptides are quite basic (FIG. 1). A.A. 331–391 contains 21 basic residues and 6 acidic residues giving it a predicted net charge of +15 at neutral pH. A.A. 40–89 has 14 basic and 4 acidic residues for a predicted net charge of +10 at neutral pH. To test whether non-specific effects of these charges were solely responsible for the ability of A.A. 331–391 and A.A. 40–89 to inhibit DNA-linking we sought a control peptide with a similar charge per molecule. Poly-Lysine (polyK, Sigma) with a mass distribution of 1000 to 4000 Daltons (Da) can be estimated to have an average mass of 2500 Da and an average charge per molecule of +16 at neutral pH. The ability of polyK, RNase A, and BSA to inhibit linking of DNAs containing two EBNA1-binding sites by NΔ360, a derivative of EBNA1 with one linking domain, was determined (Table 3). The concentration of polyk required to inhibit linking was less than that of BSA or RNase A. PolyK, however, was less effective than A.A. 331–391 and A.A. 40–89 at inhibiting linking of DNAs containing two binding sites by NΔ360. The $K_i$ of polyK was 35 and 60-fold greater than that for A.A. 40–89 and A.A. 331–391, respectively (Table 3). These experiments demonstrate that the inhibition of DNA-linking by A.A. 331–391 and A.A. 40–89 is not mediated by their charge alone.

TABLE 3

Inhibition by various competitors of DNA-linking mediated by NΔ360 and bEBNA1[a]

| Competitor | $K_i$ against NΔ360 (nM) | $K_i$ against bEBNA1 (nM) |
| --- | --- | --- |
| A.A. 40–89 | 55 | 7,600 |
| A.A 331–391 | 30 | 3,300 |
| poly-Lysine | 1,900 | 11,000 |
| Rnase A | 30,000 | >42,000 |
| BSA | >8,800 | >8,800 |

[a]The ability of 6.5 nM of dimers of either NΔ360 or bEBNA1 to link 20 fmols of a DNA with two EBNA1-binding sites was measured in the absence of competitor as well as in the presence of a range of concentrations of the indicated competitors. The concentration of competitor which inhibits linking to 50% of that in its absence ($K_i$) was determined. The highest concentrations of RnaseA and BSA tested were 42,000 and 8,800 nM, respectively.

Linking of DNAs containing two EBNA1-binding sites by bEBNA1 is more resistant to competition than is linking by NΔ360. bEBNA1, which has all three linking domains, links DNAs containing two EBNA1-binding sites almost twice as efficiently as does NΔ360, which has only one linking domain (28). Linking of DNAs containing two EBNA1-binding sites by bEBNA1 was inhibited by A.A. 40–89 and A.A. 331–391 (Table 3). The $K_i$s of A.A. 40–89 and A.A. 331–391 for linking by bEBNA1 were respectively 140- and 110-fold higher than for linking by NΔ360. Even at the highest concentrations tested, the peptides did not displace bEBNA1 from binding site-specifically to the labeled DNA (data not shown). Inhibition of DNA-linking by the peptides therefore does not result from a competition for DNA-binding. The linked complexes formed by bEBNA1 and the two binding site DNA were also 6-fold more resistant to polyK than similar complexes formed by NΔ360 (Table 3). bEBNA1-mediated linking of DNAs with two binding sites was insensitive to RNase A and BSA in the range of concentrations tested (Table 3).

Discussion

We have used gel shift assays to study the mechanism of DNA-linking by EBNA1 and its derivative NΔ360. We had shown previously that EBNA1 in excess of that required to bind all the EBNA1-binding sites in a reaction inhibited linking in that reaction (28). Competition by excess EBNA1 could be detected in the presence of a 40-fold excess of competitor DNA fragments. The competing protein was in excess relative to the DNA-bound protein, but not relative to the competing DNA. This finding indicated that protein:protein interactions could mediate DNA-linking. The competition was hypothesized to be mediated by the linking domains of proteins not bound to DNA interacting with the linking domains of proteins bound to DNA, thereby disrupting links between DNA-bound proteins. One prediction of this hypothesis is that only proteins with linking domains would compete with DNA-linking. An extension of this proposal is that linking domains alone would compete with DNA-linking.

Figure 2:
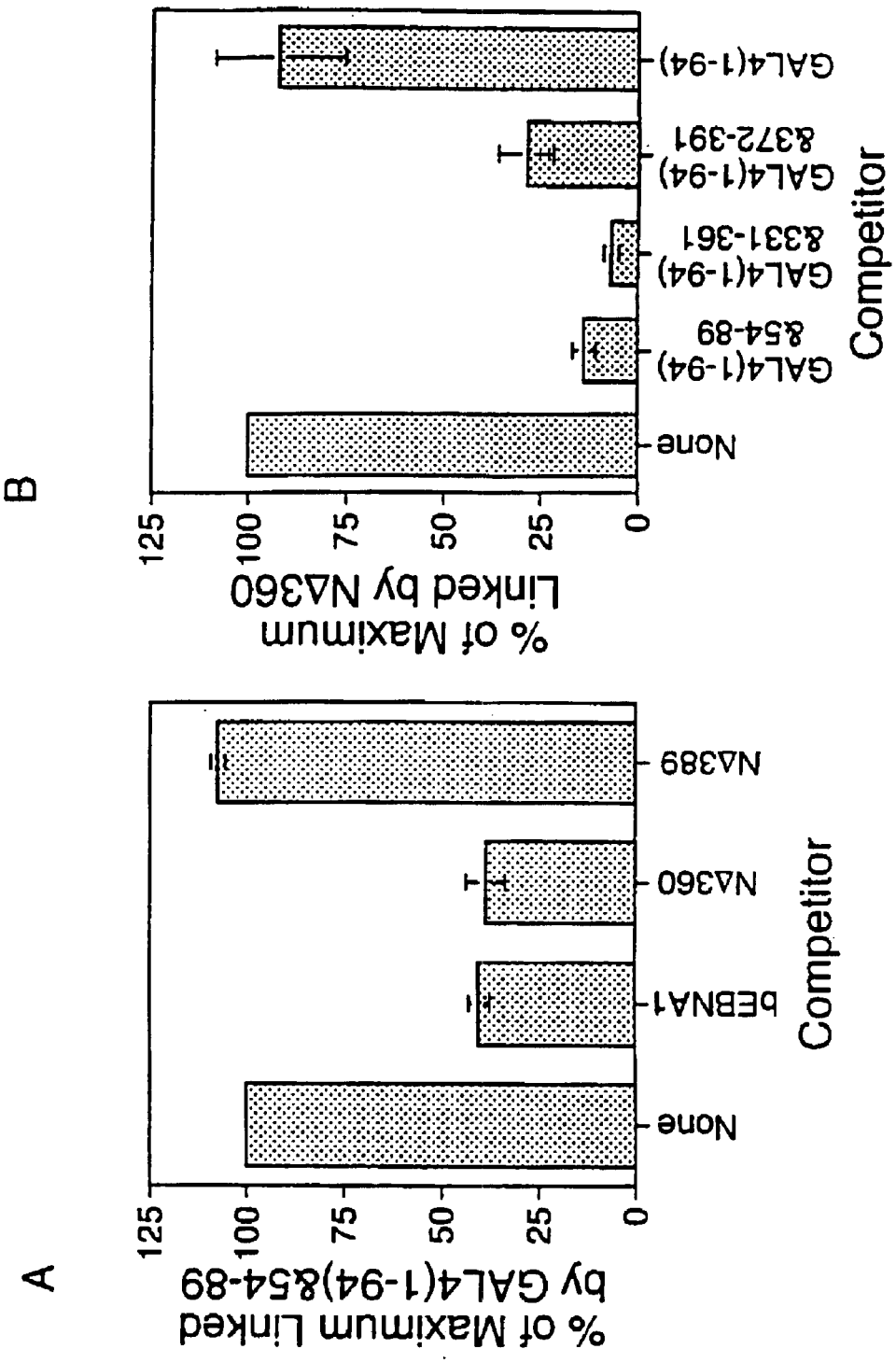
FIGS. 2A and B are graphs comparing the percentage of the maximum linked by GAL4 (1–94) & 54–89 (FIG. 2A) or NΔ360 (FIG. 2B) in the presence of competitors.

These predictions have been tested and confirmed. Only proteins which contained linking domains could inhibit DNA-linking when provided in excess (FIG. 2). DNA-linking by GAL4(1–94)&54–89 could be inhibited by bEBNA1 and NΔ360, but not by NΔ389. DNA-linking by NΔ360 could be inhibited by GAL4(1–94)&54–89, GAL4 (1–94)&331–361, and GAL4(1–94)&372–391, but not by GAL4(1–94). Because proteins with DNA-linking domains inhibit linking and derivatives without linking domains do not inhibit linking, it is likely that the linking domains themselves are mediating this inhibition. Proteins competed similarly whether they contained the same or different linking domain(s) than that of the protein with which they were competing. bEBNA1, which contains amino acids 54 to 89, and NΔ360, which lacks amino acids 54 to 89, could compete similarly for linking by GAL4(1–94)&54–89 (FIG. 2A). GAL4 fused to linking domains of EBNA1 competed equally well with DNA-linking by NΔ360 whether the fusion contained the same or a different linking domain than found in NΔ360 (FIG. 2B). These observations indicate that EBNA1's linking domains can interact heterotypically with one another.

Two peptides (A.A. 40–89 and A.A. 331–391, FIG. 1) which together contain all three of the identified linking domains inhibit DNA-linking by EBNA1. Each of these peptides can also bind non-specifically to DNA. The percentage of a DNA with two EBNA1-binding sites linked by NΔ360 could be halved by a 5-fold excess of A.A. 331–391 relative to NΔ360 (FIGS. 3A and 3B). At this concentration of A.A. 331–391 (30 nM), the poly(dI)•poly(dC) used as a competitor DNA was present in greater than 10-fold molar excess. Similarly, A.A. 40–89 could mediate a 50% inhibition of linking at 55 nM. The peptides can efficiently inhibit linking at concentrations within 10-fold of the concentration of NΔ360-peptide concentrations far less than that of the competitor DNA. These results indicate that inhibition of linking by the peptides is mediated by interactions with NΔ360 rather than nucleic acids.

We compared the ability of control proteins (BSA, RNase A and polyK) to inhibit DNA-linking by NΔ360 (Table 3). The ability of NΔ360 to link DNAs containing two EBNA1-binding sites was reduced only to 80% by 8.8 μM BSA. Linking could be inhibited to 50% by 30 μM RNase A. Approximately 1000-fold more RNase A than A.A. 331–391 was required to reduce linking by 50%. A.A. 40–89 and A.A. 331–391 each are basic peptides with predicted net charges of +10 and +15 at neutral pH, respectively. The ability of polyk with a similar charge per peptide to compete with linking mediated by NΔ360 was significantly greater than BSA or RNase A, but significantly less than A.A. 40–89 or A.A. 331–391 (Table 3). Linking could be inhibited to 50% by 1.9 μM polyk, a 35 or 60-fold higher concentration than that required for similar inhibition by A.A. 40–89 or A.A. 331–391, respectively. This result demonstrates that the inhibition of NΔ360-mediated DNA-linking by A.A. 40–89 and A.A. 331–391 may be mediated in part by nonspecific affects of their charge, but specific affects of their sequence or structure also contribute to their inhibitory activity.

Figure 3:
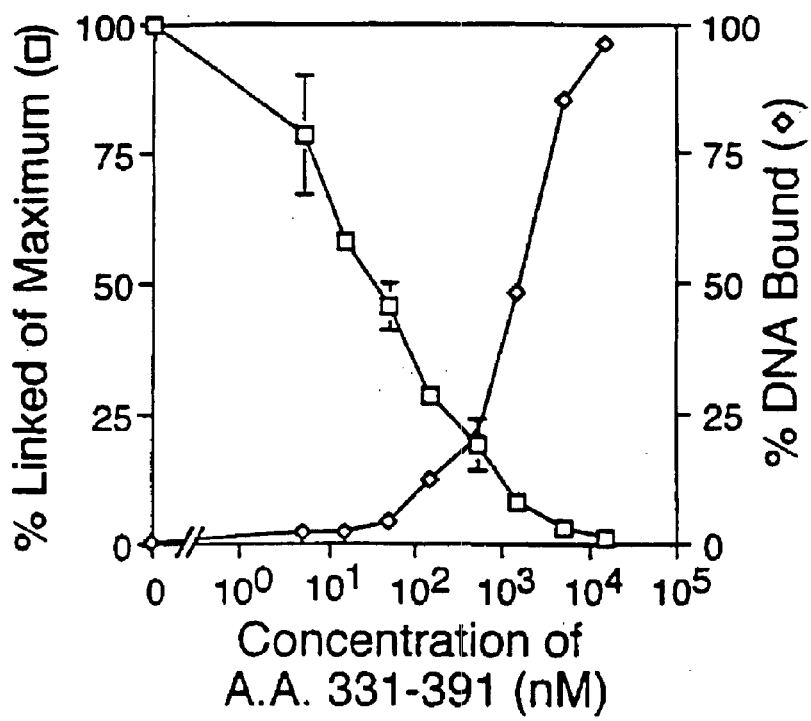
FIG. 3B is a plot of the percentage linked of maximum versus concentration of amino acid 331–391 and of the % DNA bound by amino acid 331–391 alone.
FIG. 3C is a graph of the percentage linked of maximum versus concentration of amino acid 40–89 and of the % DNA bound by amino acids 40–89 alone.
Figure 3:
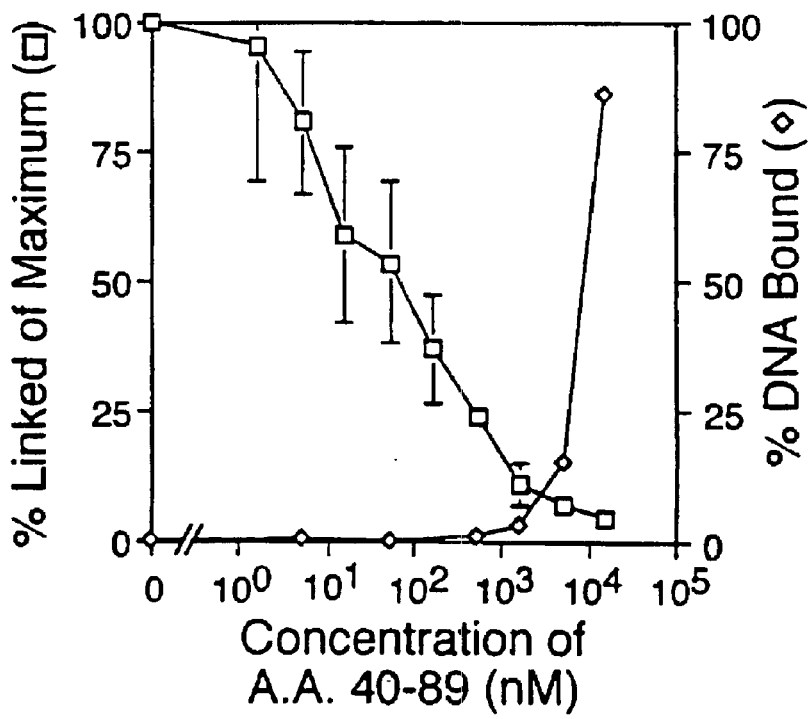

The efficiency with which DNAs are linked by EBNA1 likely reflects the valency of the complexes formed by the DNA and EBNA1. NΔ360, which has one of three linking domains of EBNA1, links greater than 95% of DNAs with ten EBNA1-binding sites (28), but only 12% of DNAs with two EBNA1-binding sites (FIG. 3). A.A. 331–391 competes for linking by NΔ360 of the ten binding site DNA approximately 0.3% as effectively as for linking of the two binding site DNA (data not shown). bEBNA1, which has all three linking domains, links DNAs containing two EBNA1-binding sites approximately twice as efficiently as NΔ360. A.A. 40–89 and A.A. 331–391 compete approximately 1% as effectively with linking of a DNA with two binding sites by bEBNA1 as they do for linking of it by NΔ360 (Table 3). The greater valency of contacts between linking domains within efficiently linked complexes presumably underlies the greater resistance of these complexes to being dissolved by peptides containing linking domains. The estimated concentration of EBNA1 in a nucleus with a five micron diameter is one millimolar (35). Assuming looping of oriP is important for EBNA1-dependent activities of oriP, the large number of EBNA1-binding sites in FR may be necessary to stabilize looping to DS in the presence of such high concentrations of EBNA1.

Observations described in the introduction support the assertion that DNA-linking contributes to the activation of transcription and replication by EBNA1. That EBNA1 is likely to link DNA in vivo at orip also supports this contention. Evidence for linking in vivo is indirect but strong. The length of oriP (1.8 kbp or 0.6 μm for B-form DNA) dictates that both FR and DS, and the EBNA1 bound to them, are confined to a maximum volume of approximately 0.1 femtoliters. Therefore, the concentration of EBNA1-binding sites at oriP is minimally 300 nM. EBNA1 occupies all of its binding sites at oriP for at least the majority of the cell cycle (36). In vitro, DNAs bound by EBNA1 are linked at concentrations far less than 300 nM. In FIG. 4, lane 4, 7 fmols of DNA is bound by EBNA1; therefore, the maximum concentration of occupied EBNA1-binding sites is 0.6 nM, and linking is readily detected. Because the concentration of binding sites at oriP is approximately 500-fold higher, linking likely occurs in vivo.

Interactions between linking domains are mediated by specific sequences or Structures of the linking domains. It is a distinct possibility that specific interactions between the linking domains of EBNA1 and other proteins also occur. Twenty amino acids of EBNA1 are sufficient to inhibit specifically linking of DNA by EBNA1 (GAL4(1–94) &372–391, FIG. 2). Smaller molecules may also be effective inhibitors of linking domain interactions. EBV is associated with many diseases including several malignancies. In all of these diseases EBNA1 is expressed in infected cells and sometimes only EBNA1 is expressed. Therefore, small molecules which inhibit EBNA1's functions, such as DNA-linking, would be clinically useful.

References

1. Adams, A. (1987) *J. Virol.* 61:1743–1746.
2. Yates, J. L. and Guan, N. (1991) *J. Virol.* 65:483–488.
3. Sugden, B. and Warren, N. (1988) *Mol. Biol. Med.* 5:84–94.
4. Kirchmaier, A. L. and Sugden, B. (1995) *J. Virol.* 69:1280–1283.
5. Reisman, D., Yates, J. and Sugden, B. (1985) *Mol. Cell. Biol.* 5:1822–1832.
6. Lupton, S. and Levine, A. J. (1985) *Mol. Cell. Biol.* 5:2533–2542.
7. Yates, J., Warren, N., Reisman, D. and Sugden, B. (1984) *Proc. Natl. Acad. Sci. USA* 81:3806–3810.
8. Ambinder, R. F., Shah, W. A., Rawlins, D. R., Hayward, G. S. and Hayward, S. D. (1990) *J. Virol.* 64:2369–2379.
9. Ambinder, R. F., Mullen, M., Chang, Y.-N., Hayward, G. S. and Hayward, S. D. (1991) *J. Virol.* 65:1466–1478.
10. Inoue, N., Harada, S., Honma, T., Kitamura, T. and Yanagi, K. (1991) *Virol.* 182:84–93.
11. Chen, M.-R., Middledorp, J. M. and Hayward, S. D. (1993) *J. Virol.* 67:4875–4885.
12. Bochkarev, A., Barwell, J. A., Pfuetzner, R. A., Bochkareva, E., Frappier, L. and Edwards, A. M. (1996) *Cell* 84:791–800.
13. Rawlins, D. R., Milman, G., Hayward, S. D. and Hayward, G. S. (1985) *Cell* 42:859–868.
14. Jones, C. H., Hayward, D. and Rawlins, D. R. (1989) *J. Virol.* 63:101–110.
15. Baer, R., Bankier, A. T., Biggin, M. D., Deininger, P. L., Farrell, P. J., Gibson, T. J., Hatfull, G., Hudson, G. S., Satchwell, S. C., Seguin, C., Tuffnell, P. S. and Barrell, B. G. (1984) *Nature* 310:207–211.
16. Sugden, B. and Warren, N. (1989) *J. Virol.* 63:2644–2649.
17. Gahn, T. A. and Sugden, B. (1995) *J. Virol.* 69:2633–2636.
18. Puglielli, M. T., Desai, N. and Speck, S. H. (1997) *J. Virol.* 71:120–128.
19. Yates, J. L. and Camiolo, S. M. (1988) *Cancer Cells* 6:197–205.
20. Polvino-Bodnar, M. and Schaffer, P. A. (1992) *Virol.* 187:591–603.
21. Su, W., Middleton, T., Sugden, B. and Echols, H. (1991) *Proc. Natl. Acad. Sci. USA* 88:10870–10874.
22. Frappier, L. and O'Donnell, M. (1991) *Proc. Natl. Acad. Sci. USA* 88:10875–10879.
23. Frappier, L. and O'Donnell, M. (1991) *J. Biol. Chem.* 266:7819–7826.
24. Middleton, T. and Sugden, B. (1992) *J. Virol.* 66:489–495.
25. Kirchmaier, A. L. and Sugden, B. (1997) *J. Virol.* 71:1766–1775.
26. Goldsmith, K., Bendell, L. and Frappier, L. (1993) *J. Virol.* 67:3418–3426.
27. Frappier, L., Goldsmith, K. and Bendell, L. (1994) *J. Biol. Chem.* 269:1057–1062.
28. Mackey, D., Middleton, T. and Sugden, B. (1995) *J. Virol.* 69:6199–6208.
29. Gahn, T. A. and Schildkraut, C. L (1989) *Cell* 58:527–535.
30. Middleton, T. and Sugden, B. (1994) *J. Virol.* 68:4067–4071.
31. Lillie, J. W. and Green, M. R. (1989) *Nature* (London) 338:39–44.
32. Sambrook, J., Fritsch, E. F. and Maniatis (1989) *Molecular Cloning: A Laboratory Manual,* 2nd Ed., Cold Spring Harbor Laboratory, Cold Spring Harbor, N.Y.
33. Miller, G. and Lipman, M. (1973) *Proc. Natl. Acad. Sci. USA* 70:190–194.
34. Laine, A. and Frappier, L. (1995) *J. Biol. Chem.* 270:30914–30918.
35. Sternås, L., Middleton, T. and Sugden, B. (1990) *J. Virol.* 64:2407–2410.
36. Hsieh, D.-J., Camiolo, S. M. and Yates, J. L. (1993) *EMBO J.* 12:4933–4944.

We claim:

1. A method of screening candidate molecules for the ability to disrupt viral looping/linking factors comprising:
   (a) adding a candidate molecule to a mammalian cell culture;
   (b) providing a control mammalian cell culture without the candidate molecule, wherein the cell cultures of both (a) and (b) comprise viral looping/linking factors, wherein the factors comprise DNA-binding proteins that can self-associate, and nucleic acid molecules comprising at least two binding sites for the factors, wherein the sites are linked by a looping/linking factor;
   (c) allowing said candidate molecule to interact with the viral looping/linking factor present in the mammalian cell culture of step (a); and
   (d) directly analyzing the factor for inhibition by the candidate molecule and comparing the result to the results using the control culture, wherein the candidate molecule inhibits protein:protein self-associate between factors as demonstrated by the factor being unable to mediate linking in the presence of the candidate molecule.

2. The method of claim 1 wherein the looping/linking factor is EBNA1.

3. The method of claim 1 wherein the factor binding sites are on a plasmid.

4. A method of screening candidate molecules for the ability to disrupt viral looping/linking factors comprising:
   (a) adding a candidate molecule to a mammalian cell culture;
   (b) providing a control mammalian cell culture without the candidate molecule, wherein the cell cultures of both (a) and (b) comprise viral looping/linking factors, wherein the factors comprise DNA-binding proteins that can self-associate, and nucleic acid molecules comprising at least two binding sites for the factors, wherein the sites are linked by a looping/linking factor;
   (c) allowing said candidate molecule to interact with the viral looping/linking factor present in the mammalian cell culture of step (a); and
   (d) analyzing the factor for inhibition by the candidate molecule and comparing the result to the results using the control culture, wherein the candidate molecule inhibits protein:protein self-associate between factors as demonstrated by the factor being unable to mediate linking in the presence of the candidate molecule, wherein the analysis of step (d) is a gel shift assay.

5. A method of screening candidate molecules for the ability to disrupt viral looping/linking factors comprising:
   (a) adding a candidate molecule to a mammalian cell culture;
   (b) providing a control mammalian cell culture without the candidate molecule, wherein the cell cultures of both (a) and (b) comprise viral looping/linking factors, wherein the factors comprise DNA-binding proteins that can self-associate, and nucleic acid molecules comprising at least two binding sites for the factors, wherein the sites are linked by a looping/linking factor;
   (c) allowing said candidate molecule to interact with the viral looping/linking factor present in the mammalian cell culture of step (a); and
   (d) analyzing the factor for inhibition by the candidate molecule and comparing the result to the results using the control culture, wherein the candidate molecule inhibits protein:protein self-associate between factors as demonstrated by the factor being unable to mediate linking in the presence of the candidate molecule, wherein the analysis of step (d) is a promoter activation assay.

* * * * *